US011541559B2

United States Patent
Lujan et al.

(10) Patent No.: US 11,541,559 B2
(45) Date of Patent: Jan. 3, 2023

(54) CUTTING SYSTEM FOR SOFT MATERIALS USING REPLACEABLE BLADES

(71) Applicant: BOISE STATE UNIVERSITY, Boise, ID (US)

(72) Inventors: Trevor Lujan, Boise, ID (US); Sean Nelson, Meridian, ID (US); Madison Wale, Boise, ID (US); Danielle Siegel, Boise, ID (US); Jaremy Creechley, Laramie, WY (US)

(73) Assignee: Boise State University, Boise, ID (US)

( * ) Notice: Subject to any disclaimer, the term of this patent is extended or adjusted under 35 U.S.C. 154(b) by 0 days.

(21) Appl. No.: 17/234,606

(22) Filed: Apr. 19, 2021

(65) Prior Publication Data

US 2021/0323045 A1    Oct. 21, 2021

Related U.S. Application Data

(60) Provisional application No. 63/011,458, filed on Apr. 17, 2020.

(51) Int. Cl.
*B26B 5/00*     (2006.01)
*B26B 29/00*    (2006.01)
*B26B 9/02*     (2006.01)
*A61B 17/322*   (2006.01)
*B26F 1/26*     (2006.01)

(52) U.S. Cl.
CPC .............. *B26B 5/008* (2013.01); *B26B 5/006* (2013.01); *B26B 9/02* (2013.01); *B26B 29/00* (2013.01); *A61B 2017/3225* (2013.01); *B26F 1/26* (2013.01)

(58) Field of Classification Search
CPC .... B26B 5/00; B26B 9/00; B26B 9/02; B26B 5/006; B23D 19/065; B26D 3/10
USPC .......................... 83/451, 657, 333; 76/107.8
See application file for complete search history.

(56) References Cited

U.S. PATENT DOCUMENTS

| | | | | |
|---|---|---|---|---|
| 3,292,643 A | * | 12/1966 | Pryde .................... | B26B 21/14 30/47 |
| 3,407,496 A | * | 10/1968 | Pomper .................. | B26B 21/28 30/49 |
| 3,412,464 A | * | 11/1968 | Keck ..................... | B65D 85/00 30/40 |
| 4,250,786 A | * | 2/1981 | Bleich .................... | B26F 1/44 83/699.41 |
| 5,176,061 A | * | 1/1993 | Mano ..................... | B26F 1/44 83/684 |
| 5,208,982 A | * | 5/1993 | Ferruzza, Jr. ......... | B26B 21/522 30/49 |

(Continued)

*Primary Examiner* — Kenneth E Peterson
*Assistant Examiner* — Richard D Crosby, Jr.
(74) *Attorney, Agent, or Firm* — Parsons Behle & Latimer

(57) ABSTRACT

A system may include a blade die, a first clamping caul positioned on a first side of the blade die, and a second clamping caul positioned on a second side of the blade die. A molding surface of the blade die and a molding surface of the first clamping caul may be configured to bend a first interchangeable blade positioned therebetween into a first shape in response to a first compression force. A second molding surface of the blade die and a molding surface of the second clamping caul may be configured to bend a second interchangeable blade positioned therebetween into a second shape in response to a second compression force.

20 Claims, 6 Drawing Sheets

(56) References Cited

U.S. PATENT DOCUMENTS

| | | | | |
|---|---|---|---|---|
| 5,221,249 | A * | 6/1993 | Simpson | B31F 1/10 493/396 |
| 6,792,840 | B2 * | 9/2004 | Myers | B26D 7/025 83/458 |
| 7,703,367 | B1 * | 4/2010 | Bayless | B26D 3/26 83/687 |
| 2001/0029822 | A1 * | 10/2001 | Schlueter, Jr. | B29C 66/8242 83/130 |
| 2017/0072579 | A1 * | 3/2017 | Reis | B26D 3/26 |

\* cited by examiner

700 ↘

702 — Receive a first interchangeable blade between a blade die and a first clamping caul, where the blade die includes a first molding surface and a second molding surface, and where the first clamping caul includes a third molding surface

704 — Receive a second interchangeable blade between the blade die and a second clamping caul, where the second clamping caul comprises a fourth molding surface

706 — Simultaneously generate a first compression force between the first molding surface and the third molding surface and a second compression force between the second molding surface and the fourth molding surface, in response to tightening of a nut onto a tightening bolt passing through the blade die, the first clamping caul, and the second clamping caul

708 — Bend the first interchangeable blade into a first shape between the first molding surface and the third molding surface in response to the first compression force

710 — Bend the second interchangeable blade into a second shape between the second molding surface and the fourth molding surface in response to a second compression force

FIG. 7

CUTTING SYSTEM FOR SOFT MATERIALS USING REPLACEABLE BLADES

CROSS-REFERENCE TO RELATED APPLICATIONS

This application claims the benefit of U.S. Provisional Patent Application No. 63/011,458, filed on Apr. 17, 2020, and entitled "Cutting System for Soft Materials Using Replaceable Blades," the contents of which are incorporated by reference herein in their entirety.

GOVERNMENT LICENSE RIGHTS

This invention was made with government support under grant no. P20GM109095 awarded by the National Institutes of Health and grant no. 1554353 awarded by the National Science Foundation. The government has certain rights in the invention.

FIELD OF THE DISCLOSURE

This disclosure is generally related to the field of cutting and, in particular, to a cutting system for soft materials using replaceable blades.

BACKGROUND

Tensile tests characterize the mechanical properties of soft materials, such as biological tissue. Data from tensile tests may be used to quantify the material strength of connective and epithelial tissues and to determine the effect of microstructure, disease, and therapy on tissue function. To ensure the validity and reproducibility of tensile tests, the test specimens, called coupons, may be designed to have a proper geometry within specified tolerances. International test standards of many conventional materials specify the use of dumbbell shaped coupons that promote failure in a region of uniform tensile stress, called the gauge section. By distributing the compressive forces needed to securely grip the specimen, the dumbbell shape reduces the risk of premature failure at or near the grips, where the stress state is more complex than simple tension.

The two most common methods for cutting test coupons are by using a scalpel and a cutting guide or by using a custom fabricated steel punch. Although using scalpels and cutting guides may provide an inexpensive, low-maintenance method that can be quickly implemented, the resulting coupon geometry is operator dependent and may be prone to large inter- and intra-specimen variations in dimensions. Conversely, custom fabricated steel punches can provide repeatable and accurate coupon geometry, but they are expensive, require considerable time to fabricate, and need periodic maintenance to sharpen the cutting edge. Sharp cutting blades may eliminate defects along the coupon edge that potentially influence material behavior. For these reason, American Society for Testing and Materials (ASTM) International standards indicate that dumbbell-shaped dies shall at all times be sharp and free of nicks. A need therefore exists to develop a novel cutting device for soft materials that overcomes these stated limitations, including the enablement of simple blade maintenance and replacing, and thereby facilitates a broad adoption of standardized test methods for tensile testing.

SUMMARY

In an embodiment, a system includes a blade die having a first molding surface and a second molding surface. The system further includes a first clamping caul positioned on a first side of the blade die, where the first clamping caul has a third molding surface that is complementary to the first molding surface. The system also includes a second clamping caul positioned on a second side of the blade die, where the second clamping caul has a fourth molding surface that is complementary to the second molding surface. The first molding surface and the third molding surface are configured to bend a first interchangeable blade positioned therebetween into a first shape in response to a first compression force between the first molding surface and the third molding surface. The second molding surface and the fourth molding surface are configured to bend a second interchangeable blade positioned therebetween into a second shape in response to a second compression force between the second molding surface and the fourth molding surface.

In some embodiments, the first interchangeable blade is a razor blade and the second interchangeable blade is a razor blade. In some embodiments, the first shape and the second shape, together, define a dumbbell shape. In some embodiments, a shape of the first molding surface and a complementary shape of the third molding surface reduce lateral translation between the first molding surface and the third molding surface and guide lateral alignment of the first clamping caul and the blade die during application of the first compression force. A shape of the second molding surface and a complementary shape of the fourth molding surface reduce lateral translation between the second molding surface and the fourth molding surface and guide lateral alignment of the second clamping caul and the blade die during application of the second compression force.

In some embodiments, the blade die includes a first ledge positioned adjacent to the first molding surface, the first ledge configured to receive the first interchangeable blade thereon and to transfer a striking force from a bottom surface of the blade die to the first interchangeable blade. The blade die may further include a second ledge positioned adjacent to the second molding surface, the second ledge configured to receive the second interchangeable blade thereon and to transfer the striking force from the bottom surface of the blade die to the second interchangeable blade.

In some embodiments, the system includes a tightening bolt passing through the blade die, the first clamping caul, and the second clamping caul, and a nut configured to attach to the tightening bolt, where tightening the nut onto the tightening bolt simultaneously generates the first compression force and the second compression force. In some embodiments, the tightening bolt and nut are enabled to be tightened manually. In some embodiments, the system includes a first washer between the nut and the first clamping caul, and a second washer between a head of the tightening bolt and the second clamping caul.

In some embodiments, the blade die, the first clamping caul, and the second clamping caul form a cutting assembly. In some embodiments, the system includes a protective lid configured to enclose a top portion of the cutting assembly. In some embodiments, the protective lid includes a protrusion configured to prevent rotation of a nut while the protective lid is positioned on the cutting assembly and while a tightening bolt is tightened into the nut. In some embodiments, the system further includes a cutting guide comprising at least two alignment members configured to guide the cutting assembly during cutting of a soft material. In some embodiments, the protective lid, the blade die, the first clamping caul, and the second clamping caul are formed using a 3-dimensional printing process. In some embodiments, the first interchangeable blade, the second interchangeable blade, or both include slots formed therein. In some embodiments, the first interchangeable blade has a bent shape before being positioned between the blade die and the first clamping caul, and the second interchangeable blade has a bent shape before being positioned between the blade die and the second clamping caul.

In an embodiment, a method includes receiving a first interchangeable blade between a blade die and a first clamping caul. The method further includes receiving a second interchangeable blade between the blade die and a second clamping caul, where the blade die comprises a first molding surface and a second molding surface, where the first clamping caul comprises a third molding surface, and where the second clamping caul comprises a fourth molding surface. The method also includes bending the first interchangeable blade into a first shape between the first molding surface and the third molding surface in response to a first compression force between the first molding surface and the third molding surface. The method includes bending the second interchangeable blade into a second shape between the second molding surface and the fourth molding surface in response to a second compression force between the second molding surface and the fourth molding surface.

In some embodiments, the method includes transferring a striking force from a bottom surface of the blade die to the first interchangeable blade via a first ledge positioned adjacent to the first molding surface, and transferring the striking force from the bottom surface of the blade die to the second interchangeable blade via a second ledge positioned adjacent to the second molding surface. In some embodiments, the method includes simultaneously generating the first compression force and the second compression force in response to tightening of a nut onto a tightening bolt passing through the blade die, the first clamping caul, and the second clamping caul.

In some embodiments, the blade die, the first clamping caul, and the second clamping caul form a cutting assembly. In some embodiments, the method includes receiving a protective lid onto the cutting assembly, where the protective lid includes a protrusion configured to prevent rotation of a nut while the protective lid is positioned on the cutting assembly. In some embodiments, the method includes at least one of the following: forming at least one slot in the first interchangeable blade, the second interchangeable blade, or both; and bending the first interchangeable blade, the second interchangeable blade, or both before receiving the first interchangeable blade between the molding die and the first clamping caul and before receiving the second interchangeable blade between the molding die and the second clamping caul.

BRIEF DESCRIPTION OF THE DRAWINGS

FIG. 7 is a flowchart depicting a method for cutting.

Figure 1:
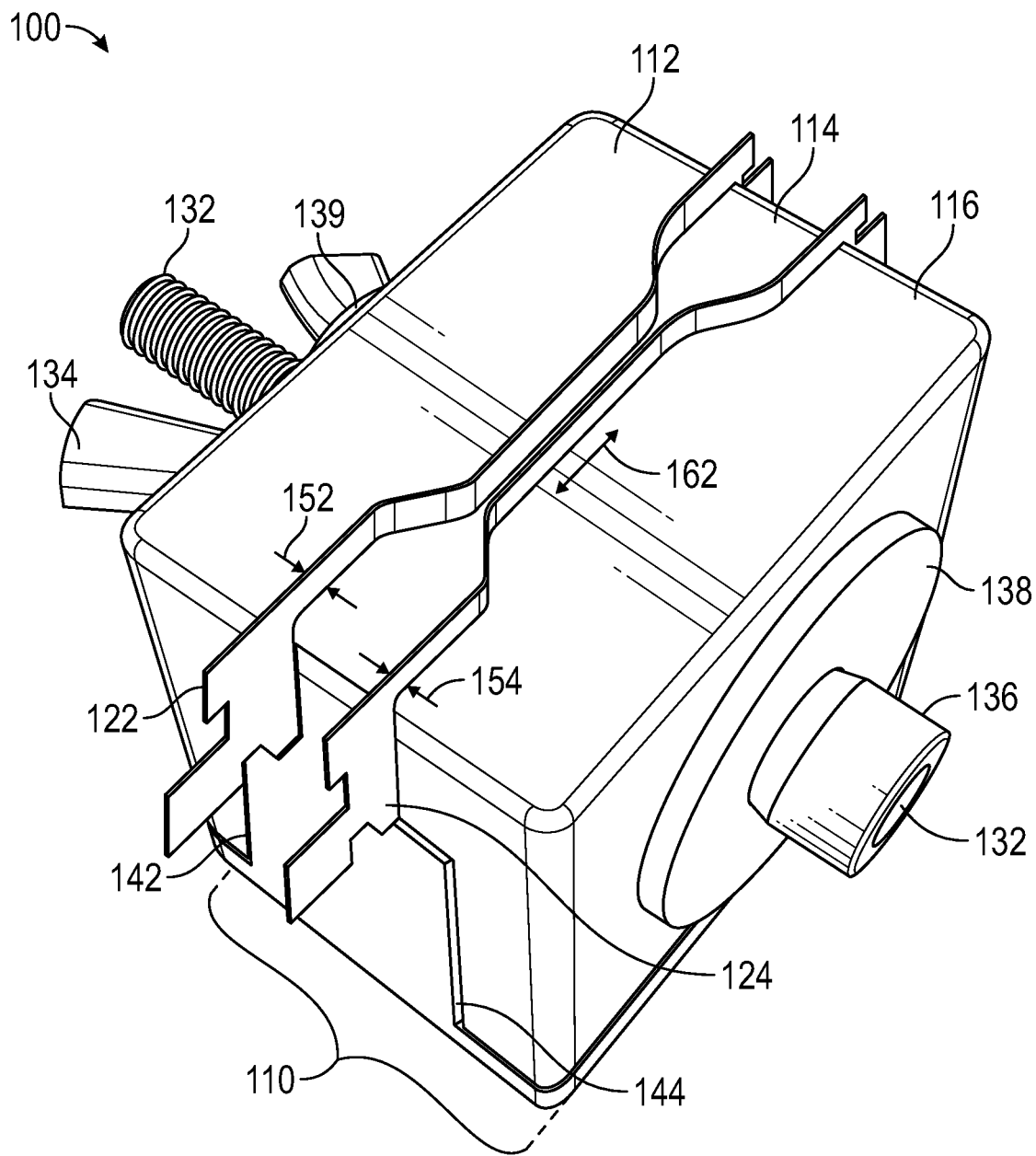
FIG. 1 is a perspective view of an embodiment of a cutting system 100 for soft materials.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the scope of the disclosure.

DETAILED DESCRIPTION

Referring to FIG. 1, an embodiment of a cutting system 100 for soft materials is depicted. The system 100 may include a first clamping caul 112, a blade die 114, and a second clamping caul 116, which, together, may form a cutting assembly 110. The first clamping caul 112 may be positioned on a first side 142 of the blade die 114 and the second clamping caul 116 may be positioned on a second side 144 of the blade die 114. The clamping cauls 112 and the blade die 114 may include 3-D printed parts.

A first interchangeable blade 122 may be positioned between the first clamping caul 112 and the blade die 114. A second interchangeable blade 124 may be positioned between the second clamping caul 116 and the blade die 114. A first compression force, represented by the arrows 152, may bend the first interchangeable blade into a first shape and a second compression force, represented by the arrows 154, may bend the second interchangeable blade 124 into a second shape. As shown in FIG. 1, the shapes of the first interchangeable blade 122 and the second interchangeable blade 124 may define a dumbbell shape. The interchangeable blades 122, 124 may include razor blades and may be formed from flexible steel, or another type of metal.

The system 100 may include a tightening bolt 132 passing through the clamping cauls 112, 116 and the blade die 114. A nut 134 may be positioned opposite a head 136 of the tightening bolt 132. The nut 134 may be configured to attach to the tightening bolt 132. As the nut 134 is tightened onto the tightening bolt 132, the first compression force 152 and the second compression force 154, may be simultaneously generated, thereby bending the interchangeable blades 122, 124 between the clamping cauls 112, 116, and the blade die 114 into their respective shapes. A first washer 139 between the nut 134 and the first clamping caul 112 and a second washer 138 between the head 136 of the tightening bolt 132 and the second clamping caul 116 may assist in distributing a force applied by the tightening bolt 132 and the nut 134. As shown in FIG. 1, the nut 134 may be a wingnut. The tightening bolt 132 may be configured to be tightened by a tool, such as a hex key, wrench, or another type of leveraged tool. As the nut 134 is tightened onto the tightening bolt 132, complementary shapes of the clamping cauls 112, 116 and the blade die 114 may reduce or prevent lateral translation, represented by the arrows 162, therebetween.

The system 100, together may be approximately 1-inch× 0.75 inches×0.75 inches and may be configured to be operated manually. A benefit of the system 100 is that the interchangeable blades 122, 124 may be removed and replaced with new blades as opposed to fixed blade cutters or stamps that may require sharpening or other maintenance. Thus, the interchangeable blades 122, 124 may be kept sharp by exchanging them for new blades. Other advantages of the system 100 may include a fast fabrication time due to the 3-dimensional printing of the components, a low material cost, good accuracy (which may be within 5% of targeted values), and an ability to scale coupon dimensions for specific tissues and experiments. By providing an economical and reliable technique to acquire dumbbell-shaped coupons from soft tissue, the system 100 can support the standardization of proper test methods for biomechanical tensile testing. Other benefits may exist.

Figure 2:
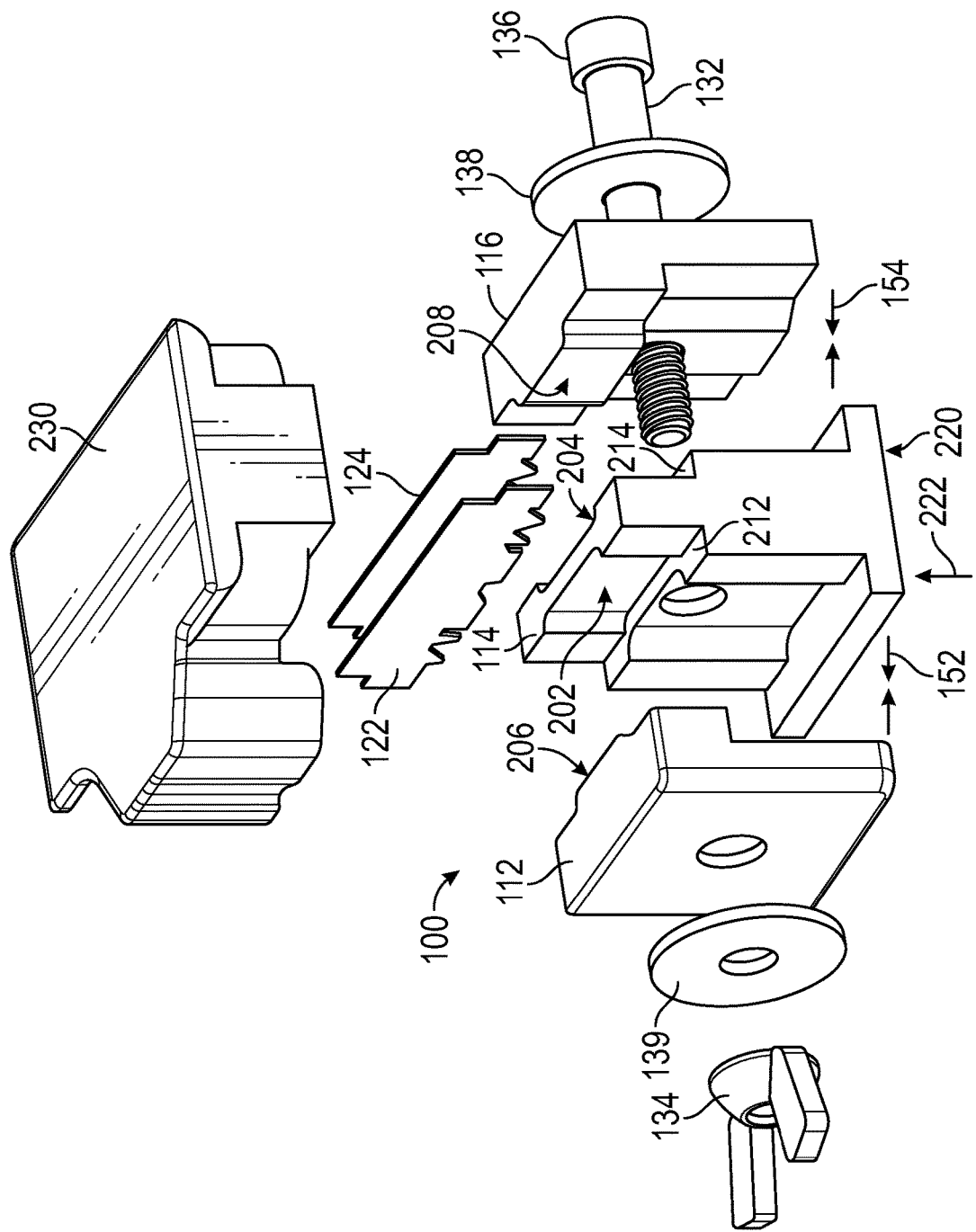
FIG. 2 is an exploded view of an embodiment of a cutting system 100 for soft materials.

Referring to FIG. 2, an exploded view of the system 100 is depicted along with a protective lid 230. The protective lid may also be considered an additional part of the system 100. The blade die 114 may include a first molding surface 202 and a second molding surface 204, the first clamping caul 112 may be have a third molding surface 206, the second clamping caul 116 may have a fourth molding surface 208. The molding surfaces 202, 204, 206, 208 may bend, and otherwise shape, the interchangeable blades 122, 124 as the nut 134 is tightened onto the tightening bolt 132. For example, when the nut 134 is tightened onto the tightening bolt 132, the nut 134 may press against the first washer 139 and the head 136 of the tightening bolt 132 may press against the second washer 138. The washers 138, 139 may, in turn, press respectively against the first clamping caul 112 and the second clamping caul 116, thereby simultaneously generating the first compression force 152 and the second compression force 154.

In response to the first compression force 152, the first molding surface 202 and the third molding surface 206 may bend the first interchangeable blade 122, which may be positioned therebetween as shown in FIG. 1, into a first shape. The second molding surface 204 and the fourth molding surface 208 may bend the second interchangeable blade 124 positioned therebetween into a second shape in response to the second compression force 154. A shape of the first molding surface 202 may be complementary of the shape of the third molding surface 206. The complementary shapes may reduce lateral translation between the first molding surface 202 and the third molding surface 206 and may guide lateral alignment of the first clamping caul 112 and the blade die 114 during application of the first compression force 152. Likewise, a shape of the second molding surface 204 may be complementary of the shape of the fourth molding surface 208, which may reduce lateral translation between the second molding surface 204 and the fourth molding surface 208 and may guide lateral alignment of the second clamping 116 caul and the blade die 114 during application of the second compression force 154.

The blade die 114 may include a first ledge 212 positioned adjacent to the first molding surface 202 and a second ledge 214 positioned adjacent to the second molding surface 204. The first ledge 212 may be configured to receive the first interchangeable blade 122 thereon and the second ledge 214 may be configured to receive the second interchangeable blade 124 thereon. As explained further herein, during a cutting operation, a striking force 222 may be applied to a bottom surface 220 of the blade die 114. The first ledge 212 may transfer the striking force 222 from the bottom surface 220 of the blade die 114 to the first interchangeable blade 122 and the second ledge 214 may transfer the striking force 222 from the bottom surface 220 to the second interchangeable blade 124.

Figure 3:
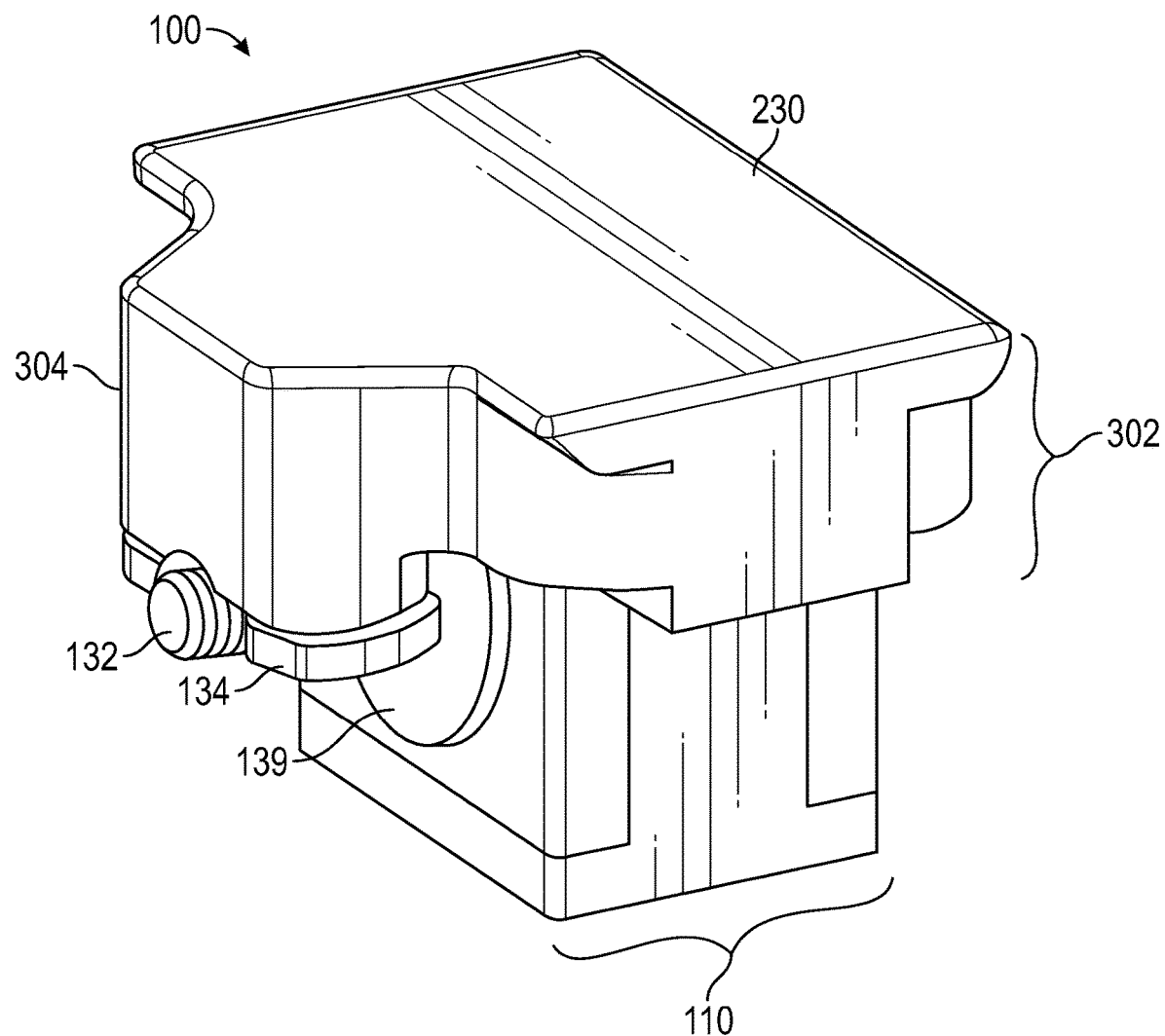
FIG. 3 is a perspective view of an embodiment of a cutting system 100 with a protective cover in place.

The protective lid 230 may be used during the blade bending process to protect a user from the interchangeable blades 122, 124. For example, referring to FIG. 3, the system 100 is depicted with the protective lid 230 enclosing a top portion 302 of the cutting assembly 110. The protective lid 130 may assist in tightening the nut 134 onto the tightening bolt 132. For example, the protective lid may include protrusion 304 that contacts the nut 134, thereby preventing the nut 134 from rotating while the protective lid 230 is in place. In some cases, the nut 134 may be retained in a horizontal configuration, as shown in FIG. 3. In other cases, a vertical slot may cut into the protrusion 134, thereby retaining the nut in a vertical configuration. A tool, such as a hex key, or another type of wrench, may be used to rotate the tightening bolt 132. Because the nut 134 is prevented from rotating, it may be tightened onto the tightening bolt 132. The protective lid 230 may enable a user to tighten the tightening bolt 132, and thereby bend the interchangeable blades (e.g., as shown in FIG. 1) without the risk of cuts or other injury. As with other parts of the system 100, the protective lid 230 may be formed through a 3-dimensional printing operation. Other advantages may exist.

Figure 4:
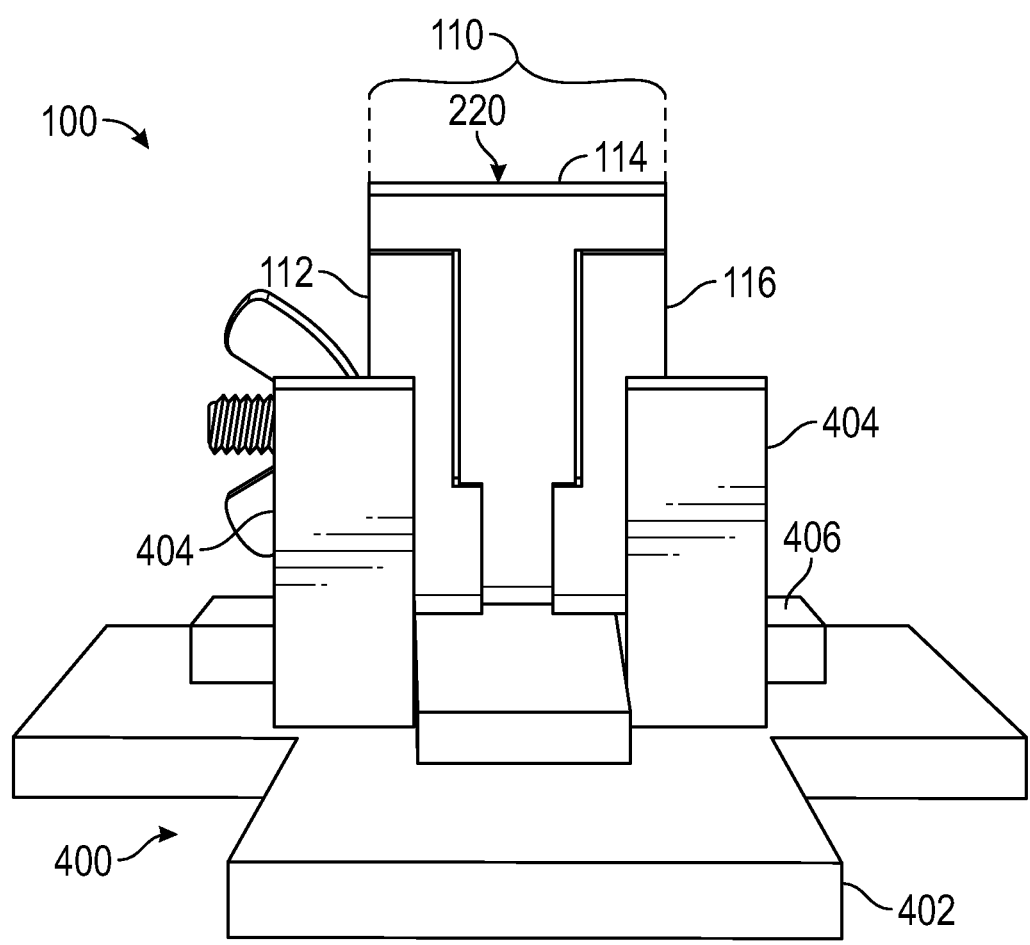
FIG. 4 is a diagram depicting an embodiment of a cutting system 100 with a cutting guide.

Referring to FIG. 4, the system 100 is depicted as used with a cutting guide 400. The cutting guide 400 may include a base 402, a protective layer 406, and at least alignment members 404 configured to guide the cutting assembly 110 during a cutting process. During use, a sample to be cut may be positioned on the protective layer 406. The cutting assembly 110 may be inverted and placed between the alignment members 404. The alignment members 404 may prevent lateral movement of the cutting assembly 110. Although not visible in FIG. 4, the interchangeable blades may be put in contact with the sample while the cutting assembly 110 is inverted. A striking force may be applied to the bottom surface 220 of the blade die 114. The striking force may cause the interchangeable blades to cut through the sample, thereby creating a coupon having the shape imposed on the blades by the clamping cauls 112, 116 and the blade die 114.

Figure 5:
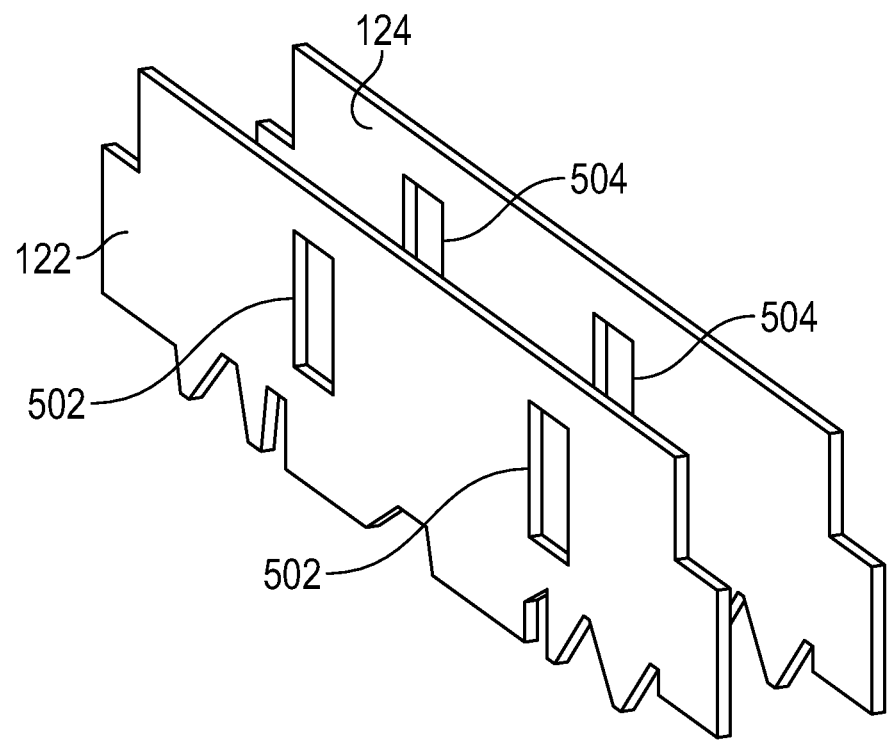
FIG. 5 is a perspective view of interchangeable blades having slots defined therein.
Figure 6:
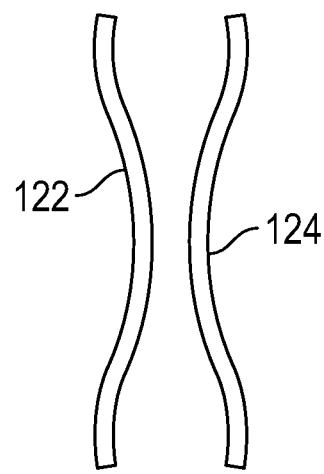
FIG. 6 is a top view of interchangeable blades having a pre-bent shape.

Various measures may be taken to ensure the proper bending of the interchangeable blades 122, 124. For example, referring to FIG. 5, the first interchangeable blade 122 may include one or more slots 502 formed therein. The slots 502 may enable the interchangeable blade 122 to flex easier along portions of the blade that are bent when compressed between the first clamping caul 112 and the blade die 114. This may enable the blades to be shaped with less force and to retain their shape. Likewise, the second interchangeable blade 124 may include slots 504 formed therein. As another example, referring to FIG. 6, the first interchangeable blade 122 may be pre-bent, or may otherwise have a bent shape, before being positioned between the blade die 114 and the first clamping caul 112. Likewise, the second interchangeable blade 124 may be pre-bent before being positioned between the blade die and the second clamping caul. In some cases, to the interchangeable blades 122, 124 may be pre-bent into their final shapes before being inserted between the clamping cauls 112, 116 and the blade die 114. In other cases, the interchangeable blades 122, 124 may only be roughly bent into shape and the compression force imposed by the clamping cauls 112, 116 may form them into their final shapes.

Referring to FIG. 7, a method 700 for cutting soft materials is depicted. The method 700 may include receiving a first interchangeable blade between a blade die and a first clamping caul, where the blade die includes a first molding surface and a second molding surface, and where the first clamping caul includes a third molding surface, at 702. For example, the first interchangeable blade 122 may be received between the blade die 114 and the first clamping caul 112.

The method 700 may further include receiving a second interchangeable blade between the blade die and a second clamping caul, where the second clamping caul comprises a fourth molding surface, at 704. For example, the second interchangeable blade 124 may be positioned between the blade die 114 and the second clamping caul 116.

The method 700 may also include simultaneously generating a first compression force between the first molding surface and the third molding surface and a second compression force between the second molding surface and the fourth molding surface, in response to tightening of a nut onto a tightening bolt passing through the blade die, the first clamping caul, and the second clamping caul, at 706. For example, the first compression force 152 and the second compression force 154 may be generated in response to tightening of the nut 134 onto the tightening bolt 132.

The method 700 may include bending the first interchangeable blade into a first shape between the first molding surface and the third molding surface in response to the first compression force, at 708. For example, the first interchangeable blade 122 may be bent by the first molding surface 202 and the third molding surface 206 in response to the first compression force 152.

The method may further include bending the second interchangeable blade into a second shape between the second molding surface and the fourth molding surface in response to a second compression force, at 710. For example, the second interchangeable blade 124 may be bent by the second molding surface 204 and the fourth molding surface 208 in response to the second compression force 154.

A benefit of the method 700 is that the interchangeable blades may be bent to enable coupons to be cut from soft material with a high degree of precision. Further, because the blades are interchangeable, they may be removed and replaced with new blades, which can be bent in the same way. This may eliminate the need to sharpening or provide other maintenance on the blades as may be needed for systems that used a fixed stamp for cutting. Other benefits may exist.

In practice, the ability of the disclosed system to produce coupons with desired dumbbell geometry was analyzed by varying three design factors: coupon length, neck curvature, and razor clearance. Twenty-seven punches were printed to represent the variations of the design factors. The overall length and width of the printed punches was verified using digital calipers to have an error less than 3%.

Each unique design was used to punch three specimens from neoprene rubber sheets that were 0.4 mm thick. The razor blades were replaced prior to cutting each unique design. Each specimen was imaged next to a calibration square with a digital camera that provided a conversion factor of 48.3±0.4 pixels per mm. The digital camera was fixed in a stand 70 mm above the imaging space for the duration of the experiment to ensure imaging repeatability between specimens. Images were analyzed to evaluate error in cutting specimens to their targeted dimensions. Four metrics were analyzed: mean gauge width, intra-specimen variation in gauge width, effective gauge length, and coupon symmetry.

All three design factors significantly influenced the dimensional accuracy of the dumbbell shaped coupons. In general, dimensional accuracy was best when using longer coupons with a low neck curvature and tight razor clearance. These trends were also supported by the significant interactions measured between all the design factors. Dimensional errors increased the most when increasing the neck curvature from low to high and increasing the coupon length from short to large.

Coupon symmetry was largely insensitive to device design, except that short coupons were 2-3× more symmetric in the gauge section than longer coupons, leading to overall differences in coupon asymmetry, and coupons with high neck curvature had less symmetry in the width tapered region than coupons with low neck curvature.

The dimensional accuracy of the device was tested on three bovine meniscus specimens that were layered to ~1 mm thickness. For this test, a punch design was selected with good dimensional accuracy when cutting elastomer sheets (medium-low-lax). Each bovine specimen was punched and manually preloaded in tension until the specimen was taut. Image acquisition and analysis followed the previously described procedure for the elastomer specimens. Bovine tissue exhibited greater intra-specimen variations in gauge width and had greater inter-specimen variations in gauge width and length. The only difference in symmetry was that the width tapered region of meniscus coupons was roughly 2 times more asymmetric than elastomer coupons.

Although various embodiments have been shown and described, the present disclosure is not so limited and will be understood to include all such modifications and variations as would be apparent to one skilled in the art.

What is claimed is:

1. A system comprising:
   a blade die having a first molding surface and a second molding surface;
   a first clamping caul positioned on a first side of the blade die, wherein the first clamping caul has a third molding surface that is complementary to the first molding surface;
   a second clamping caul positioned on a second side of the blade die, wherein the second clamping caul has a fourth molding surface that is complementary to the second molding surface, wherein the blade die, the first clamping caul, and the second clamping caul form a cutting assembly, wherein the first molding surface and the third molding surface are configured to bend a first interchangeable blade positioned therebetween into a first shape in response to a first compression force between the first molding surface and the third molding surface, and wherein the second molding surface and the fourth molding surface are configured to bend a second interchangeable blade positioned therebetween into a second shape in response to a second compression force between the second molding surface and the fourth molding surface, and
   a protective lid configured to enclose at least a top portion of the cutting assembly wherein the protective lid comprises a protrusion configured to contact a nut and prevent rotation of the nut while the protective lid is positioned on the cutting assembly and while a tightening bolt is tightened into the nut.

2. The system of claim 1, wherein the first interchangeable blade is a razor blade and the second interchangeable blade is a razor blade.

3. The system of claim 1, wherein the first shape and the second shape, together, define a dumbbell shape.

4. The system of claim 1, wherein a shape of the first molding surface and a complementary shape of the third molding surface reduce lateral translation between the first molding surface and the third molding surface and guide lateral alignment of the first clamping caul and the blade die during application of the first compression force, and wherein a shape of the second molding surface and a complementary shape of the fourth molding surface reduce lateral translation between the second molding surface and the fourth molding surface and guide lateral alignment of the second clamping caul and the blade die during application of the second compression force.

5. The system of claim 1, wherein the blade die comprises: a first ledge positioned adjacent to the first molding surface, the first ledge configured to receive the first interchangeable blade thereon and to transfer a striking force from a bottom surface of the blade die to the first interchangeable blade; and
    a second ledge positioned adjacent to the second molding surface, the second ledge configured to receive the second interchangeable blade thereon and to transfer the striking force from the bottom surface of the blade die to the second interchangeable blade.

6. The system of claim 1, further comprising:
a tightening bolt passing through the blade die, the first clamping caul, and the second clamping caul; and
a nut configured to attach to the tightening bolt, wherein tightening the nut onto the tightening bolt simultaneously generates the first compression force and the second compression force.

7. The system of claim 6, wherein the tightening bolt and nut are enabled to be tightened manually.

8. The system of claim 6, further comprising:
a first washer between the nut and the first clamping caul; and
a second washer between a head of the tightening bolt and the second clamping caul.

9. The system of claim 1, wherein the blade die, the first clamping caul, and the second clamping caul form a cutting assembly, the system further comprising:
a cutting guide comprising at least two alignment members configured to guide the cutting assembly during cutting of a soft material.

10. The system of claim 1, wherein the blade die, the first clamping caul, and the second clamping caul are formed using a 3-dimensional printing process.

11. The system of claim 1, wherein the first interchangeable blade, the second interchangeable blade, or both include slots formed therein.

12. The system of claim 1, wherein the first interchangeable blade has a pre-bent shape before being positioned between the blade die and the first clamping caul, and wherein the second interchangeable blade has a pre-bent shape before being positioned between the blade die and the second clamping caul, wherein the blade die and the first clamping caul bend the first interchangeable blade to a final bent shape, and wherein the blade die and the second clamping caul bend the second interchangeable blade to a final bent shape.

13. The system of claim 1, wherein the first interchangeable blade has a straight shape before being positioned between the blade die and the first clamping caul, and wherein the second interchangeable blade has a straight shape before being positioned between the blade die and the second clamping caul.

14. The system of claim 1, wherein the protrusion includes a vertical slot configured to retain the nut in a vertical configuration.

15. The system of claim 1, wherein the protective lid is configured to enable a user to tighten the tightening bolt without the risk of exposing the user to the first interchangeable blade or the second interchangeable blade.

16. A method comprising:
receiving a first interchangeable blade between a blade die and a first clamping caul;
receiving a second interchangeable blade between the blade die and a second clamping caul, wherein the blade die comprises a first molding surface and a second molding surface, wherein the first clamping caul comprises a third molding surface, and wherein the second clamping caul comprises a fourth molding surface, wherein the blade die, the first clamping caul, and the second clamping caul form a cutting assembly;
receiving a protective lid onto the cutting assembly, wherein the protective lid comprises a protrusion configured to prevent rotation of a nut while the protective lid is positioned on the cutting assembly and while a tightening bolt is tightened into the nut;
bending the first interchangeable blade into a first shape between the first molding surface and the third molding surface in response to a first compression force between the first molding surface and the third molding surface; and
bending the second interchangeable blade into a second shape between the second molding surface and the fourth molding surface in response to a second compression force between the second molding surface and the fourth molding surface.

17. The method of claim 16, wherein the first shape and the second shape, together, define a dumbbell shape.

18. The method of claim 16, further comprising:
transferring a striking force from a bottom surface of the blade die to the first interchangeable blade via a first ledge positioned adjacent to the first molding surface; and
transferring the striking force from the bottom surface of the blade die to the second interchangeable blade via a second ledge positioned adjacent to the second molding surface.

19. The method of claim 16, further comprising:
simultaneously generating the first compression force and the second compression force in response to tightening of the nut onto the tightening bolt passing through the blade die, the first clamping caul, and the second clamping caul.

20. The method of claim 16, further comprising at least one of the following:
forming at least one slot in the first interchangeable blade, the second interchangeable blade, or both; and
bending the first interchangeable blade, the second interchangeable blade, or both before receiving the first interchangeable blade between the molding die and the first clamping caul and before receiving the second interchangeable blade between the molding die and the second clamping caul.

\* \* \* \* \*